(12) United States Patent
Mallavadhani et al.

(10) Patent No.: US 8,748,658 B2
(45) Date of Patent: Jun. 10, 2014

(54) **FAST ISOLATION METHOD FOR THE NATURAL SCAFFOLD URSOLIC ACID FROM *DIOSPYROS MELANOXYLON***

(75) Inventors: Uppuluri Venkata Mallavadhani, Bhubaneswar (IN); Banita Pattnaik, Bhubaneswar (IN)

(73) Assignee: Council of Scientific and Industrial Research, New Delhi (IN)

( * ) Notice: Subject to any disclaimer, the term of this patent is extended or adjusted under 35 U.S.C. 154(b) by 589 days.

(21) Appl. No.: 13/052,556

(22) Filed: Mar. 21, 2011

(65) Prior Publication Data
US 2011/0237827 A1   Sep. 29, 2011

(30) Foreign Application Priority Data

Mar. 22, 2010 (IN) .......................... 0679/DEL/2010

(51) Int. Cl.
*C07C 61/12* (2006.01)
*C07C 61/28* (2006.01)

(52) U.S. Cl.
USPC ........................................................ 562/498

(58) Field of Classification Search
None
See application file for complete search history.

(56) References Cited

FOREIGN PATENT DOCUMENTS

| CN | 1358733 | 7/2002 |
|---|---|---|
| CN | 1508149 | 6/2004 |
| CN | 1629180 | 6/2005 |
| CN | 1733794 | 2/2006 |
| CN | 1763072 | 4/2006 |
| CN | 1923844 | 3/2007 |
| CN | 101422502 | 5/2009 |
| CN | 101544679 | 9/2009 |
| RU | 2329048 | 7/2008 |

OTHER PUBLICATIONS

Mallavadhani et al. Pharmaceutical Biology, 2001, 39(1), 20-24.*
S. Jäger et al., "Pentacyclic Triterpene Distribution in Various Plants—Rich Sources for a New Group of Multi-Potent Plant Extracts," Molecules (2009), v. 14, p. 2016-2031.
J. Liu, "Pharmacology of oleanolic acid and ursolic acid," Journal of Ethnopharmacology (1995), vol. 49, p. 57-68.
J. Liu, "Oleanolic acid and ursolic acid: Research perspectives," Journal of Ethnopharmacology (2005), vol. 100, p. 92-94.
U.V. Mallavadhani et al., "Diospyros melanoxylon Leaves: A Rich Source of Pentacyclic Triterpenes," Pharmaceutical Biology (2001), vol. 39, No. 1, p. 20-24.
L.Ramachandra Rao et al., "The Chemical Explanation of Diospyros Species," Current Science (1966), No. 18, p. 457-8.
L. Ramachandra Row et al., "Chemical Examination of Diospyros Species: part VII—Triterpenes of Leaves of D melanoxylon," Indian Journal of Chemistry (1969), vol. 7, p. 204-206.
M.G.V. Silva et al., "Variation of Ursolic Acid Content in Eight Ocimum Species from Northeastern Brazil," Molecules (2008), vol. 13, p. 2482-2487.
H.Y. Tu et al., "Ursolic acid derivatives induce cell cycle arrest and apoptosis in NTUB1 cells associated with reactive oxygen species," Bioorganic & Medicinal Chemistry (2009), vol. 17, p. 7265-7274.
S. Dev et al., Excerpt from "CRC Handbook of Terpenoids: Triterpenoids, vol. I: Acyclic, Monocyclic, Bicyclic, Tricyclic, and Tetracyclic Terpenoids," CRC Press, Inc., Boca Raton, Florida, (1989) pp. 38 and 42.
S. Dev et al., Excerpt from "CRC Handbook of Terpenoids: Triterpenoids, vol. II: Pentacyclic and Hexacyclic Triterpenoids," CRC Press, Inc., Boca Raton, Florida, (1989) pp. 287-288.
S.K. Chattopadhyay et al., Abstract of Indian patent No. IN191699, (2009) 1 page.
S.A. Shevtsov et al., Abstract of Russian patent No. SU1816346 (1996) 1 page.

* cited by examiner

*Primary Examiner* — Yevegeny Valenrod
(74) *Attorney, Agent, or Firm* — Hamre, Schumann, Mueller & Larson, P.C.

(57) ABSTRACT

The present invention relates to a process for the fast isolation of ursolic acid, a highly potent natural scaffold, from the leaves of *Diospyros melanoxylon*. The present invention also provides an improved and fast isolation process of the title compound, which is a pentacyclic triterpenic acid highly useful for the synthesis of a wide range of novel and potent bio-active molecules.

9 Claims, 1 Drawing Sheet

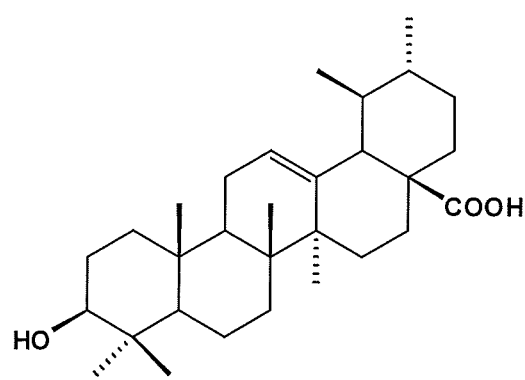

FAST ISOLATION METHOD FOR THE NATURAL SCAFFOLD URSOLIC ACID FROM DIOSPYROS MELANOXYLON

FIELD OF INVENTION

The present invention relates to a process for the fast isolation of ursolic acid, a highly potent natural scaffold, from the leaves of *Diospyros melanoxylon*. More particularly the present invention relates to an improved and fast isolation process of the title compound, which is a pentacyclic triterpenic acid highly useful for the synthesis of a wide range of novel and potent bio-active molecules.

BACK-GROUND OF INVENTION

Ursolic acid, chemically known as 3β-hydroxy-urs-12-ene-28-oic acid (FIG. 1) is a pentacyclic triterpenic acid exist widely in natural plant sources in the form of free acid or glycoside (J. Liu, *Journal of Ethnopharmacology*, 49, 57-68, 1995). Ursolic acid displaying a variety of pharmacological activities such as anti-tumor, anti-inflammatory, anti-viral and anti-oxidant activities (H. Tu et al., *Bioorganic & Medicinal Chemistry*, 17, 7265-7274, 2009) while being devoid of prominent toxicity. Hence, this triterpenic acid has been identified as a promising lead compound for the development of novel and multi-targeting bio-active molecules. Isolation of ursolic acid from natural sources involves three major steps, such as (i) Extraction of the plant source using suitable polar solvents (ii) Isolation using fractional solubility/crystallization or chromatographic methods (iii) Purification by recrystallization or repeated chromatography. Of these, the first step i.e. the extraction is the most important step and will have an impact on the total yield of the desired compound. Literature search reveals that ursolic acid found wide spread and accumulated in a number of plant species belonging to various families. It is found mostly in leaves, flowers and fruit peels of the plant species (S. Jager et al. *Molecules*, 14, 2016-2031, 2009).

The high yielding plant sources of ursolic acid are *Rosemarinus, Ocimum, Salvia, Lavendula, Coffea, Arctostaphylos* and *Diospyros* (S. Jager et al. *Molecules*, 14, 2016-2031, 2009; M. G. V. Silva et al., *Molecules*, 13, 2482-2487, 2008 and *Hand Book of Terpenoids*, Triterpeniods, Vol. I & II, SukhDev, CRC Press, Boca Raton, Fla., 1989). Among these, *Diospyros* species particularly *Diospyros melanoxylon* is endemic to Indian sub-continent. It is popularly known as Kendu and is commercially and medicinally important plant of India. In commerce, its coppiced leaves are highly valued as wrappers in bidi (cigarette) industry. The leaf trade is an important socio-economic activity of tribal of India, especially of the states of Orissa, Madhya Pradesh & Andhra Pradesh and is a good source of revenue for the Government. In Indian traditional medicine the leaves have been extensively used as diuretic, styptic, laxative, carminative and ophthalmic agent. The *D. melanoxylon* leaves have been chemically screened earlier by five research groups. However, Rao et al. (i. *Curr. Sci*, 35, 457-458, 1966 and ii. *Indian J. Chem.*, 7(3), 204-206, 1969) and Mallavadhani et al. (*Pharmaceutical Biology*, 39(1), 20-24, 2001) have only reported ursolic acid from the leaves. Rao et al. isolated ursolic acid from the alcoholic extract of the leaves from the completely grown-up tree by using derivatisation followed by fractional crystallization method in 0.24% yield. Where as Mallavadhani et al. isolated ursolic acid from ethyl acetate extract of the coppiced leaves by employing column chromatography in 0.56% yield. Most interestingly this group also found similar accumulation of ursolic acid in the brittle and powdered waste leaves generated during the bidi wrapping process. This clearly suggests that ursolic acid can be generated from the waste *D. melanoxylon* leaves with out consuming the fresh leaves. The above mentioned two isolation methods are tedious, consume lot of solvents and time.

Extensive patent search revealed that ursolic acid was earlier produced from plant sources using various methods such as i) extraction followed by acid/base treatment and repeated crystalisations (Chattopadhyay, S. K. and Koneni, V. S., Kumar, S., Tripathi, V., IN191699-B; Kozlova, L. P., Malykhin, E. V., Obut, S. M., Popov, S. A., Sheremet, O. P., RU2329048-C1; Yang, Q., Feng, H., Mi, K., CN1629180-A, CN100360551-C; Shevtsov, S. A., Raldugin, V. A., Shchukin, G. I., SU1816346-A3) ii) extraction followed by fractionation, decolorisation and crystallisation (Luo, X., Cai, X., CN1923844-A, CN100526327-C; He, C, Fan, J, CN1763072-A, CN100480257-C); iii) fermentation followed by ultra sound extraction (He, G, Ruan, H., Shen, S., Xu, B., Xu, C, Yu, H, CN101422502-A); iv) extraction by microwave/reflux followed by sedimentation, ultrafiltration, nano filtration, adsorption gel chromatography, fractionation, decolorisation (Zhou, C., Ren, X., Peng, M., CN1508149-A); v) counter current extraction or separation (Fan, M., Bian, Z., Wang, Q., CN1358733-A, CN1126757-C, He, C. F., CN1733794-A); vi) extraction followed by Sephadex LH-20 gel filtration (Wenyi, K., Yanli, S., Zhiquiang, J., Jinmei, W., CN11544679-A). These methods have drawbacks such as longer isolation times, consume large volumes of solvents, cumbersome acid/base treatments, use of expensive adsorption gels such as Sephadex, low selectivity and purity.

As ursolic acid has become "Hot Molecule" its fast isolation and availability in abundance for further developmental work is highly warranted. In view of its urgency, a novel and fast isolation process has now been developed for ursolic acid.

OBJECT OF THE INVENTION

The main object of the present invention is to provide a process for the fast isolation of ursolic acid, a highly useful natural scaffold for the development of a wide range of novel and biologically active compounds from the leaves of *Diospyros melanoxylon*.

The another object of the present invention is to provide fast isolation of ursolic acid, a highly potent natural scaffold, from the leaves of *Diospyros melanoxylon*.

SUMMARY OF INVENTION

Accordingly, the present invention provides a process for the fast isolation of ursolic acid, a highly potent natural scaffold, from the leaves of *Diospyros melanoxylon* in significant levels. One of the polar extracts containing ursolic acid has been subjected to flash chromatographic separation using a novel protocol resulted in the isolation of ursolic acid in very short time with very high purity (Single spot on TLC, $R_f$:0.3, n-Hexane-Ethyl acetate 80:20). It is the first report and new invention for obtaining the title compound in very short time.

In an embodiment of the present invention, a process for the fast isolation of ursolic acid from *Diospyros melanoxylon*, which comprises:
(I) soxhlet extraction of the powdered coppiced leaves of *Diospyros melanoxylon* with a medium polar solvent for a period in the range of 12 to 36 hrs at temperature in the range 64-780° C.;

(ii) concentrating reaction mixture as obtained in step (i) under reduced pressure using a rotary evaporator to obtain crude extract;

(iii) absorbing the crude extract as obtained in step (ii) on silica gel followed by flash chromatographic separation of the crude extract using CombiFlash chromatographic system to obtain the crude ursolic acid.

(iv) decolorisation the crude ursolic acid with charcoal in acetone solution followed by recrystallisation from a organic solvent to obtain pure colorless ursolic acid.

In another embodiment of the present invention the medium polar organic solvents used in step (i) is selected from the group consisting of ethyl acetate propyl acetate and butyl acetate.

In another embodiment of the present invention, wherein flash chromatographic system used in step (iii) for isolation of ursolic acid are selected from a glass column pumped with a continuous flow of nitrogen/air or an instrument consisting of a pump exerting a uniform pressure up to 50 psi.

In another embodiment of the present invention, wherein the CombiFlash chromatography is carried out in step (iii) with a gradient elution ratio of n-hexane and ethyl acetate in the range of 100:0, 95:5, 80:20.

In another embodiment of the present invention, wherein the CombiFlash chromatography is carried out in step (iii) with a flow rate of 10 ml/min.

In another embodiment of the present invention, wherein the flash chromatographic separation is carried out in step (iii) at pump pressure 15 psi In another embodiment of the present invention, wherein the solvent used for recrystallisation in step (iv) is methanol.

In another embodiment of the present invention, wherein pure ursolic acid is obtained in time period ranging between 5.5-8.5 hrs.

In another embodiment of the present invention, wherein yield of obtained ursolic acid is in the range of 0.25-0.60%.

BRIEF DESCRIPTION OF THE FIGURES

FIG. 1 Chemical structure of Ursolic acid (3β-Hydroxy-urs-12-ene-28-oic acid)

DETAILED DESCRIPTION OF THE INVENTION

The present invention provides the process for the fast isolation of ursolic acid, a highly useful natural scaffold for the development of a wide range of novel and biologically active compounds from the leaves of *Diospyros melanoxylon*, using extraction with any of the polar solvents and filtering followed by concentrating the various solubles under reduced pressure to obtain the crude extracts followed by flash chromatographic separation of the medium polar extract to furnish the desired ursolic acid.

The invention relates to a process for the fast isolation of ursolic acid, a highly useful natural scaffold for the development of a wide range of novel and biologically active compounds from the leaves of *Diospyros melanoxylon*, using flash chromatographic method has been disclosed. The process has the advantage due to the use of flash chromatography, as the isolation time and solvent consumption has been drastically reduced. Otherwise in the process of isolating ursolic acid by conventional and cumbersome procedures like fractional solubility/crystallizations/derivatisation or repeated column chromatographic separations. The developed method is simple and commercially viable.

One embodiment of the invention relates to a process for the fast isolation of ursolic acid, a highly useful natural scaffold for the development of a wide range of novel and biologically active compounds from the leaves of *Diospyros melanoxylon*, which comprises:—

(i) Extraction of the powdered leaves of *Diospyros melanoxylon* with various polar solvents.

(ii) Concentration of the extract under reduced pressure.

(iii) Subjecting one of the medium polar extract to flash chromatography using a specific gradient elution and collection of variable volumes of fractions to obtain crude ursolic acid.

(iv) Treatment of the above obtained ursolic acid with a decolorizing agent followed by recrystallisation from a suitable solvent system.

The following examples are given to illustrate the process of the present invention and should not be construed to limit the scope of the present invention.

Example: 1

The dark green colored ethyl acetate extract (4 gms) of the coppiced leaves of *D. melanoxylon* was adsorbed on silica gel (10 gm.) and subjected to conventional column chromatographic separation. A glass column of 900×30 mm (l×d) has been packed with 200 mesh silica gel (210 gms). Then the adsorbed material was poured into the column slowly and packed uniformly. The column was then eluted with solvents of increasing polarity of n-hexane to n-hexane ethyl acetate mixtures using a total of 9.1 liters of n-hexane and 0.8 liters ethyl acetate as per the following: Six fractions each of 250 ml of n-hexane, n-hexane-ethyl acetate (95:5) & n-hexane-ethyl acetate (90:10) and 22 fractions each of 250 ml of n-hexane-ethyl acetate (88:12) were collected. Fractions showing single spot corresponding to ursolic acid were combined and concentrated on a rotavapor followed by decolorisation with charcoal and recrystallisation from methanol afford ursolic acid as colorless amorphous powder (0.56%), m.p. 270° c. The time taken for isolation of the title compound is 30 hrs.

Example: 2

The coppiced leaves of *D. melanoxylon* were shade dried powdered and extracted (100 gm) successfully with n-hexane, ethyl acetate and methanol each 300 ml by soxhlet extraction each for 12 hrs by refluxing on a water bath. The various solubles on concentration under reduced pressure afforded the crude extracts in 1.06, 2.18, and 28.35% respectively. The co-TLC of the three extracts with the standard ursolic acid reveals that the desired compound is present only in the ethyl acetate extract (Rf.0.62, Chloroform-Methanol, 95:5).

Example: 3

The dark green colored ethyl acetate extract (4 gms) of the coppiced leaves of *D. melanoxylon* was adsorbed on silica gel (6 gms). The adsorbed material has been subjected to flash chromatographic separation using ISCO CombiFlash Chromatographic System Sg 100c. A glass column of 350×25 mm (l×d) with Teflon connectors at both ends has been packed with silica gel (30 gm) of 230-400 mesh size. Then the adsorbed material was poured in to this column slowly and packed uniformly. The column was then eluted with solvents of increasing polarity from n-hexane to ethyl acetate in a gradient mode at a flow rate of 10 ml/min at 15 psi pressure using UV detector at wavelength of 215 nm. The whole process is controlled by a PC based Peak Track software using gradient elution from 100% n-hexane to 100% ethyl acetate, 25 fractions of 100 ml capacity were collected. Fractions showing single spots corresponding to ursolic acid were combined and concentrated on a rotavapor followed by decolorisation with charcoal in acetone solution and recrystallisation from methanol afforded ursolic acid as colorless amorphous powder (0.25%), m.p. 270° C. The time taken for isolation of the title compound is 7.5 hrs.

Example: 4

The dark green colored ethyl acetate extract (4 gms) of the coppiced leaves of D. melanoxylon was subjected to flash chromatographic separation by employing the above mentioned chromatographic system with similar conditions except the gradient elution. Using a gradient elution starting from 5% ethyl acetate-hexane to 100% ethyl acetate, 5 fractions were collected with volumes ranging from 250-1000 ml. Fractions showing single spots corresponding to ursolic acid were combined and concentrated on a rotavapor followed by decolorisation with charcoal and recrystallisation from methanol afforded ursolic acid as colorless amorphous powder (0.31%), m.p. 270° C. The time taken for isolation of the title compound is 8.5 hrs.

Example: 5

The dark green colored ethyl acetate extract (4 gms) of the coppiced leaves of D. melanoxylon was subjected to flash chromatographic separation by employing the above mentioned chromatographic system with similar conditions except the gradient elution. A gradient elution starting from 20% ethyl acetate-hexane to 100% ethyl acetate, 10 fractions were collected with variable volumes (50~250 ml). Fractions showing single spots corresponding to ursolic acid were combined and concentrated on a rotavapor followed by decolorisation with charcoal and recrystallisation from methanol afforded ursolic acid as colorless amorphous powder (0.60%), m.p. 270° C. The time taken for isolation of the title compound is 5.5 hrs.

COMPARISON BETWEEN CONVENTIONAL METHODS AND PRESENT INVENTION INVOLVING FLASH CHROMATOGRAPHIC TECHNIQUE FOR THE ISOLATION OF URSOLIC ACID FROM THE PLANT EXTRACT

| Method | Silica gel | Solvents | | Time |
| --- | --- | --- | --- | --- |
| | | Hexane | Ethyl acetate | |
| Conventional Methods | 220 gm | 9.1 liters | 0.8 liters | 30 hrs |
| Present Invention | 50 gm | 1.6 liters | 0.5 liters | 5.5 hrs |

* The above figures are for separating 4 gm. of Extract

ADVANTAGES OF THE PRESENT INVENTION

Ursolic acid is obtained from the ethyl acetate extract of coppiced leaves of Diospyros melanoxylon in a maximum yield of 0.60% using CombiFlash chromatography in a very short time, which otherwise obtained by using cumbersome and time consuming derivatisation/fractional crystallization or column chromatographic methods in low yields.

Ursolic acid can be obtained from extract level to pure solid form in a maximum time period of 5.5 hrs, there by saving lot of time.

The method requires low volumes of eluents as compared to conventional gravity column chromatography, there by saving lot of money.

The method is cost effective and commercially viable.

We claim:

1. A process for fast isolation of ursolic acid from Diospyros melanoxylon, comprising:
   (i) soxhlet extraction of powdered coppiced leaves of Diospyros melanoxylon with a polar organic solvent for a period in a range of 12 to 36 hrs at a temperature in a range of 64-78° C. so as to obtain a reaction mixture;
   (ii) concentrating the reaction mixture as obtained in step (i) under reduced pressure to obtain a crude extract;
   (iii) absorbing the crude extract as obtained in step (ii) on a silica gel followed by a flash chromatographic separation of the crude extract using a CombiFlash chromatographic system to obtain a crude ursolic acid;
   (iv) decolorising the crude ursolic acid as obtained in step (iii) with charcoal in acetone solution followed by recrystallisation from an organic solvent to obtain a pure colorless ursolic acid.

2. A process as claimed in claim 1, wherein the polar organic solvent used in step (i) includes at least one selected from the group consisting of ethyl acetate propyl acetate and butyl acetate.

3. A process as claimed in claim 1, wherein the flash chromatographic system used in step (iii) is carried out in a system selected from a glass column pumped with a continuous flow of nitrogen/air and an instrument comprising a pump exerting a uniform pressure of up to 50 psi.

4. The process as claimed in claim 1, wherein the flash chromatographic separation in step (iii) is carried out with a gradient elution from 100% n-hexane to 100% ethyl acetate.

5. The process as claimed in claim 1, wherein the flash chromatographic separation in step (iii) is carried out with a flow rate of 10 ml/min.

6. The process as claimed in claim 1, wherein the flash chromatographic separation in step (iii) is carried out at a pump pressure 15 psi.

7. The process as claimed in claim 1, wherein the solvent used for recrystallization in step (iv) is methanol.

8. The process as claimed in claim 1, wherein a time period to obtain a pure ursolic acid from the crude extract obtained in (ii) is between 5.5-8.5 hrs.

9. The process as claimed in claim 1, wherein a yield for the pure ursolic acid is in a range of 0.25-0.60%.

* * * * *